US010892056B2

(12) United States Patent
Xie et al.

(10) Patent No.: US 10,892,056 B2
(45) Date of Patent: Jan. 12, 2021

(54) ARTIFICIAL INTELLIGENCE BASED ALERT SYSTEM

(71) Applicant: International Business Machines Corporation, Armonk, NY (US)

(72) Inventors: Yiting Xie, Cambridge, MA (US); Ben Graf, Charlestown, MA (US); Arkadiusz Sitek, Ashland, MA (US)

(73) Assignee: International Business Machines Corporation, Armonk, NY (US)

( * ) Notice: Subject to any disclaimer, the term of this patent is extended or adjusted under 35 U.S.C. 154(b) by 139 days.

(21) Appl. No.: 16/193,396

(22) Filed: Nov. 16, 2018

(65) Prior Publication Data

US 2020/0160993 A1 May 21, 2020

(51) Int. Cl.
*G06K 9/00* (2006.01)
*G16H 50/20* (2018.01)
(Continued)

(52) U.S. Cl.
CPC .............. *G16H 50/20* (2018.01); *G06F 40/20* (2020.01); *G06T 7/0012* (2013.01); *G16H 15/00* (2018.01); *G16H 30/40* (2018.01)

(58) Field of Classification Search
CPC ........ G16H 50/20; G16H 50/00; G16H 15/00; G16H 30/40; G16H 30/20; G16H 30/00;
(Continued)

(56) References Cited

U.S. PATENT DOCUMENTS 5,807,256 A * 9/1998 Taguchi ................ G06F 19/321
600/300
2011/0276346 A1 11/2011 Reiner
(Continued)

OTHER PUBLICATIONS

Bunnik, Eline M. et al., "Ethical framework for the detection, management and communication of incidental findings in imaging studies, building on an interview study of researchers' practices and perspectives", BMC Medical Ethics, 2017, Published Online Feb. 6, 2017, 15 pages.
(Continued)

*Primary Examiner* — Jose L Couso
(74) *Attorney, Agent, or Firm* — Francis Lammes; Stephen J. Walder, Jr.; William J. Stock

(57) ABSTRACT

A mechanism is provided to implement an artificial intelligence (AI) based alert mechanism system for alerting a medical professional of potential inaccuracies in medical image analysis. Responsive to receiving a medical image of a patient and a radiology report associated with the medical image, the AI based alert mechanism analyzes the radiology report to identify medical findings detected by the medical professional and analyzes the medical image to detect one or more medical findings associated with the medical image. Responsive to the AI based alert mechanism identifying one or more medical findings, the AI based alert mechanism compares the identified medical findings to those medical findings identified in the radiology report. Responsive to the AI based alert mechanism identifying a discrepancy between the identified medical findings to those in the radiology report, the AI based alert mechanism generates an alert to the medical professional who generated the radiology report.

20 Claims, 4 Drawing Sheets

(51) Int. Cl.
*G16H 30/40* (2018.01)
*G16H 15/00* (2018.01)
*G06T 7/00* (2017.01)
*G06F 40/20* (2020.01)

(58) Field of Classification Search
CPC ........ G16H 10/60; G16H 10/00; G16H 10/40; G16H 80/00; G06F 40/20; G06F 40/154; G06F 16/337; G06F 16/219; G06F 19/321; G06F 19/3418; G06F 19/36; G06F 19/00; G06F 19/30; G06F 19/32; G06F 19/325; G06F 19/34; G06F 30/27; G06T 7/0012; G06T 7/0014; G06T 7/0016; G06T 2200/24; G06T 2207/30004; G06T 2207/30008; G06T 2207/30016; G06T 2207/30052; G06T 2207/30061; G06T 2207/30068; G06T 2207/10124; G06T 2207/20084; G06T 2207/20081; G06T 2207/10081; G06T 2207/30096; G06T 2207/30036; G06T 2207/30056; G06T 2207/30168; G06T 2210/41; G06Q 10/10; G06Q 50/24; A61B 5/4312; A61B 5/441; A61B 5/4547; A61B 5/7267; A61B 5/743; A61B 5/745; A61B 5/4836; A61B 34/10; G06K 9/6262; G06K 9/00496; G06K 9/6288; G06K 9/62; G06K 9/6257; G06K 9/6263; G06K 9/627; G06K 9/6256; G06K 2209/051; G06K 2209/05; G06K 2209/053; G06K 2209/055; G06N 20/00; G06N 3/08; G06N 3/02; G06N 3/0454; G06N 3/084; G06N 5/046
See application file for complete search history.

(56) References Cited

U.S. PATENT DOCUMENTS

| | | |
|---|---|---|
| 2014/0278448 A1 | 9/2014 | Sadeghi et al. |
| 2014/0358585 A1* | 12/2014 | Reiner .................. G06F 16/219 705/3 |
| 2015/0025909 A1* | 1/2015 | Hayter, II ............ G06F 19/321 705/3 |
| 2016/0012187 A1 | 1/2016 | Zasowski et al. |
| 2016/0364857 A1 | 12/2016 | Reicher et al. |
| 2019/0189268 A1* | 6/2019 | Stoval, III ............. A61B 6/502 |
| 2020/0043600 A1* | 2/2020 | Glottmann ............ G06F 40/154 |
| 2020/0126678 A1* | 4/2020 | Douglas ................. G16H 30/40 |

OTHER PUBLICATIONS

Dheensa, Sandi et al., "Management of Incidental Findings in Clinical Genomic Sequencing Studies", Management of Incidental Findings in Clinical Genomic Sequencing Studies, Jan. 2016, 7 pages.

Mabotuwana, Thusitha et al., "A Generalizable Approach to Extract Radiology Follow-Up Recommendations with Associated Anatomy", SIIM 2017, Society for Imaging Informatics in Medicine, Pittsburgh, PA, Jun. 1-3, 2017, 5 pages.

* cited by examiner

ARTIFICIAL INTELLIGENCE BASED ALERT SYSTEM

BACKGROUND

The present application relates generally to an improved data processing apparatus and method and more specifically to computer mechanisms for alerting a medical professional of potential inaccuracies in medical image analysis using artificial intelligence.

Decision-support systems exist in many different industries where human experts require assistance in retrieving and analyzing information. An example is a diagnosis system employed in the healthcare industry. Diagnosis systems can be classified into systems that use structured knowledge, systems that use unstructured knowledge, and systems that use clinical decision formulas, rules, trees, or algorithms. The earliest diagnosis systems used structured knowledge or classical, manually constructed knowledge bases. The Internist-I system developed in the 1970s uses disease-finding relations and disease-disease relations. The MYCIN system for diagnosing infectious diseases, also developed in the 1970s, uses structured knowledge in the form of production rules, stating that if certain facts are true, then one can conclude certain other facts with a given certainty factor. DXplain, developed starting in the 1980s, uses structured knowledge similar to that of Internist-I, but adds a hierarchical lexicon of findings.

Iliad, developed starting in the 1990s, adds more sophisticated probabilistic reasoning where each disease has an associated a priori probability of the disease (in the population for which Iliad was designed), and a list of findings along with the fraction of patients with the disease who have the finding (sensitivity), and the fraction of patients without the disease who have the finding (1-specificity).

In 2000, diagnosis systems using unstructured knowledge started to appear. These systems use some structuring of knowledge such as, for example, entities such as findings and disorders being tagged in documents to facilitate retrieval. ISABEL, for example, uses Autonomy information retrieval software and a database of medical textbooks to retrieve appropriate diagnoses given input findings. Autonomy Auminence uses the Autonomy technology to retrieve diagnoses given findings and organizes the diagnoses by body system. First CONSULT allows one to search a large collection of medical books, journals, and guidelines by chief complaints and age group to arrive at possible diagnoses. PEPID DDX is a diagnosis generator based on PEPID's independent clinical content.

Clinical decision rules have been developed for a number of medical disorders, and computer systems have been developed to help practitioners and patients apply these rules. The Acute Cardiac Ischemia Time-Insensitive Predictive instrument (ACI-TIPI) takes clinical and ECG features as input and produces probability of acute cardiac ischemia as output to assist with triage of patients with chest pain or other symptoms suggestive of acute cardiac ischemia. ACI-TIPI is incorporated into many commercial heart monitors/defibrillators. The CaseWalker system uses a four-item questionnaire to diagnose major depressive disorder. The PKC Advisor provides guidance on 98 patient problems such as abdominal pain and vomiting.

SUMMARY

This Summary is provided to introduce a selection of concepts in a simplified form that are further described herein in the Detailed Description. This Summary is not intended to identify key factors or essential features of the claimed subject matter, nor is it intended to be used to limit the scope of the claimed subject matter.

In one illustrative embodiment, a method is provided, in a data processing system comprising at least one processor and at least one memory, the at least one memory comprising instructions executed by the at least one processor to cause the at least one processor to implement an artificial intelligence (AI) based alert mechanism system for alerting a medical professional of potential inaccuracies in medical image analysis. The method comprises receiving, by the AI based alert mechanism, a medical image of a patient and a radiology report associated with the medical image. The also method comprises analyzing, by the AI based alert mechanism, the radiology report to identify medical findings detected by the medical professional; and analyzing, by the AI based alert mechanism, the medical image to detect one or more medical findings associated with the medical image. Moreover, responsive to the AI based alert mechanism identifying one or more medical findings, the method comprises comparing, by the AI based alert mechanism, the identified medical findings to those medical findings identified in the radiology report. Additionally, responsive to the AI based alert mechanism identifying a discrepancy between the identified medical findings to those medical findings identified in the radiology report, the method comprises generating, by the AI based alert mechanism, an alert to the medical professional who generated the radiology report.

In other illustrative embodiments, a computer program product comprising a computer useable or readable medium having a computer readable program is provided. The computer readable program, when executed on a computing device, causes the computing device to perform various ones of, and combinations of, the operations outlined above with regard to the method illustrative embodiment.

In yet another illustrative embodiment, a system/apparatus is provided. The system/apparatus may comprise one or more processors and a memory coupled to the one or more processors. The memory may comprise instructions which, when executed by the one or more processors, cause the one or more processors to perform various ones of, and combinations of, the operations outlined above with regard to the method illustrative embodiment.

These and other features and advantages of the present invention will be described in, or will become apparent to those of ordinary skill in the art in view of, the following detailed description of the example embodiments of the present invention.

BRIEF DESCRIPTION OF THE DRAWINGS

The invention, as well as a preferred mode of use and further objectives and advantages thereof, will best be understood by reference to the following detailed description of illustrative embodiments when read in conjunction with the accompanying drawings, wherein.

DETAILED DESCRIPTION

Figure 1:
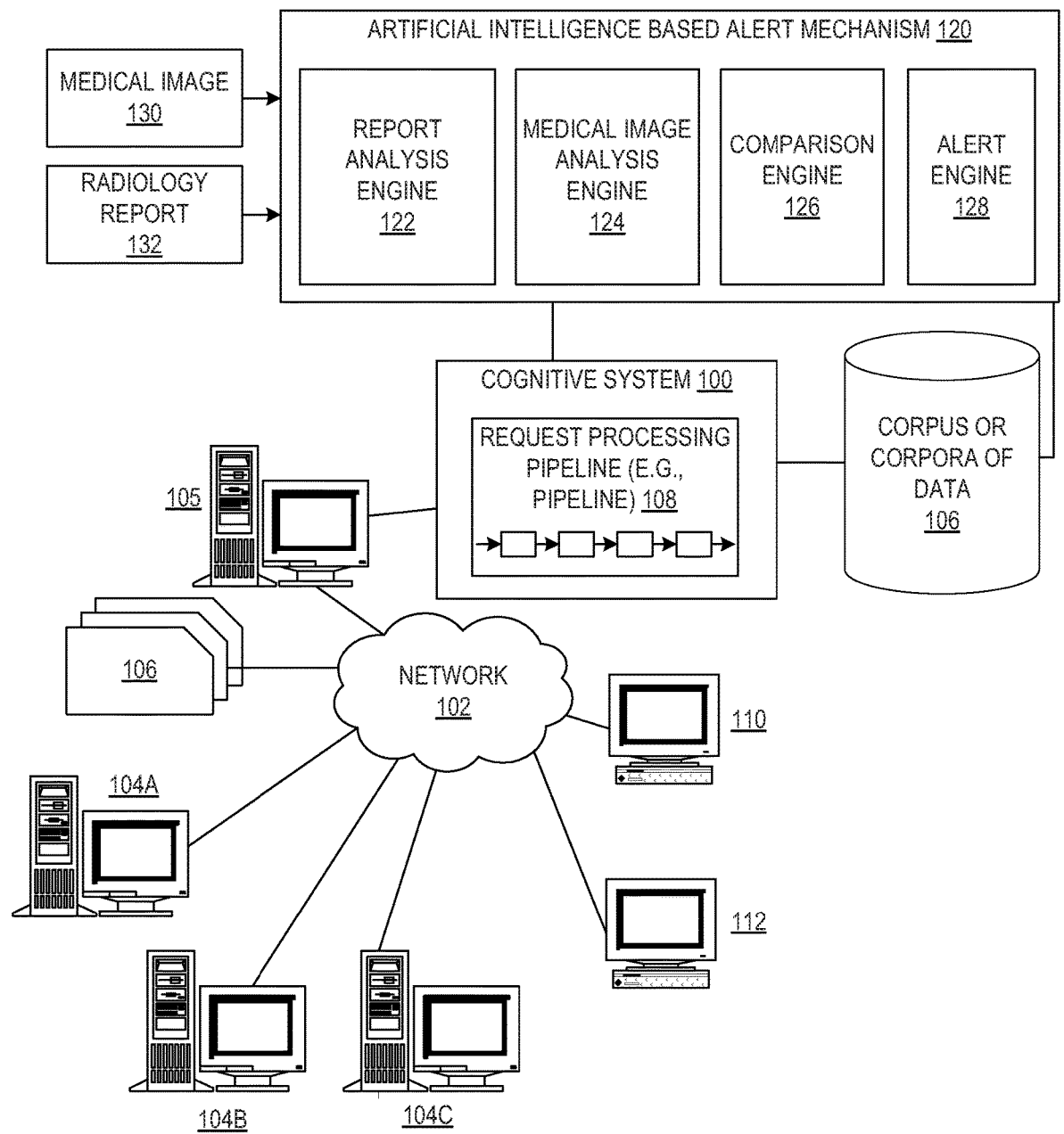
FIG. 1 depicts a schematic diagram of one illustrative embodiment of a cognitive healthcare system in a computer network.

With more precise imaging techniques, such as computerized axial tomography (CT) scan, magnetic resonance imaging (MRI) scan, ultrasound (U/S) scan, positron emission tomography (PET) scan, X-ray scan, or the like, come new imperfections. Inaccuracies in the field today include missed findings, diagnostic errors, or the like. Problems that arise in the area of imaging may result in incorrect diagnoses, incorrect treatment, issues with liability, or the like. Today, about 24% of image readings result in incidental findings (31% in CT scans), about 30% lead to missed findings, and about 3-5% of readings yield a diagnostic error, for example, a false positive or a false negative. Specifically, errors and miss rates are higher in X-Ray and CT scans.

With the advent of artificial intelligence (AI) in healthcare, opportunities arise for the use of intelligent computing devices and machines in assessing patient information without human input or assistance. In order to decrease the number of inaccuracies, i.e. missed findings, diagnostic errors, or the like, the illustrative embodiments provide an AI based alert mechanism that alerts a medical professional of potential inaccuracies in medical image analysis. In the illustrative embodiments, the AI based alert mechanism acquires a medical image of a patient and a radiology report associated with the same medical image, such as a radiology report interpreted by a radiologist per a standard of care. The AI based alert mechanism analyzes the radiology reports using for example, a natural language processing (NLP) algorithm, to identify medical findings detected by the medical professional. The AI based alert mechanism further analyzes the same medical image using, for example, an image analytics algorithm, which is trained to detect diseases, conditions, or the like, associated with the particular medical image. Responsive to the AI based alert mechanism identifying one or more medical findings, the AI based alert mechanism compares the AI identified medical findings to those medical findings identified in the radiology report. Responsive to identifying a discrepancy in the two medical findings, the AI based alert mechanism generates an alert that is passed to the medical professional who generated the radiology report. Thus, the AI based alert mechanism identifies potential inaccuracies in medical image analysis using a combination of AI medical image analysis and radiology report analysis.

Before beginning the discussion of the various aspects of the illustrative embodiments in more detail, it should first be appreciated that throughout this description the term "mechanism" will be used to refer to elements of the present invention that perform various operations, functions, and the like, A "mechanism," as the term is used herein, may be an implementation of the functions or aspects of the illustrative embodiments in the form of an apparatus, a procedure, or a computer program product. In the case of a procedure, the procedure is implemented by one or more devices, apparatus, computers, data processing systems, or the like. In the case of a computer program product, the logic represented by computer code or instructions embodied in or on the computer program product is executed by one or more hardware devices in order to implement the functionality or perform the operations associated with the specific "mechanism." Thus, the mechanisms described herein may be implemented as specialized hardware, software executing on general purpose hardware, software instructions stored on a medium such that the instructions are readily executable by specialized or general purpose hardware, a procedure or method for executing the functions, or a combination of any of the above.

The present description and claims may make use of the terms "a," "at least one of," and "one or more of" with regard to particular features and elements of the illustrative embodiments. It should be appreciated that these terms and phrases are intended to state that there is at least one of the particular feature or element present in the particular illustrative embodiment, but that more than one can also be present. That is, these terms/phrases are not intended to limit the description or claims to a single feature/element being present or require that a plurality of such features/elements be present. To the contrary, these terms/phrases only require at least a single feature/element with the possibility of a plurality of such features/elements being within the scope of the description and claims.

Moreover, it should be appreciated that the use of the term "engine," if used herein with regard to describing embodiments and features of the invention, is not intended to be limiting of any particular implementation for accomplishing and/or performing the actions, steps, processes, etc., attributable to and/or performed by the engine. An engine may be, but is not limited to, software, hardware and/or firmware or any combination thereof that performs the specified functions including, but not limited to, any use of a general and/or specialized processor in combination with appropriate software loaded or stored in a machine readable memory and executed by the processor. Further, any name associated with a particular engine is, unless otherwise specified, for purposes of convenience of reference and not intended to be limiting to a specific implementation. Additionally, any functionality attributed to an engine may be equally performed by multiple engines, incorporated into and/or combined with the functionality of another engine of the same or different type, or distributed across one or more engines of various configurations.

In addition, it should be appreciated that the following description uses a plurality of various examples for various elements of the illustrative embodiments to further illustrate example implementations of the illustrative embodiments and to aid in the understanding of the mechanisms of the illustrative embodiments. These examples intended to be non-limiting and are not exhaustive of the various possibilities for implementing the mechanisms of the illustrative embodiments. It will be apparent to those of ordinary skill in the art in view of the present description that there are many other alternative implementations for these various elements that may be utilized in addition to, or in replacement of, the examples provided herein without departing from the spirit and scope of the present invention.

As noted above, the present invention provides mechanisms for alerts a medical professional of potential inaccuracies in medical image analysis. The AI based alert mechanism acquires a medical image of a patient and a radiology report associated with the same medical image. The AI based alert mechanism analyzes the radiology reports to identify medical findings detected by the radiologist. The AI based alert mechanism further analyzes the same medical image to detect diseases, conditions, or the like, associated with the particular medical image. Responsive to the AI based alert mechanism identifying one or more medical findings, the AI based alert mechanism compares the AI identified medical findings to those medical findings identified in the radiology report. Responsive to identifying a discrepancy in the two medical findings, the AI based alert mechanism generates an alert that is passed to the medical professional who generated the radiology report.

Figure 2:
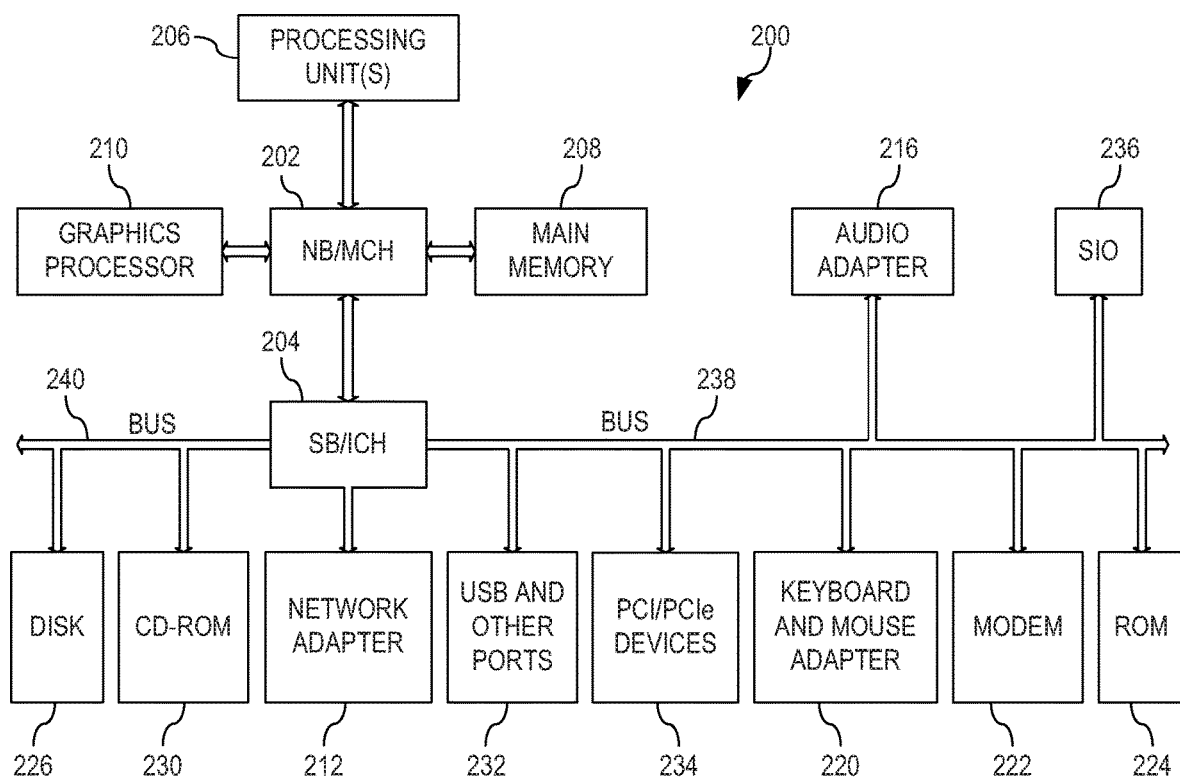
FIG. 2 is a block diagram of an example data processing system in which aspects of the illustrative embodiments are implemented.
Figure 3:
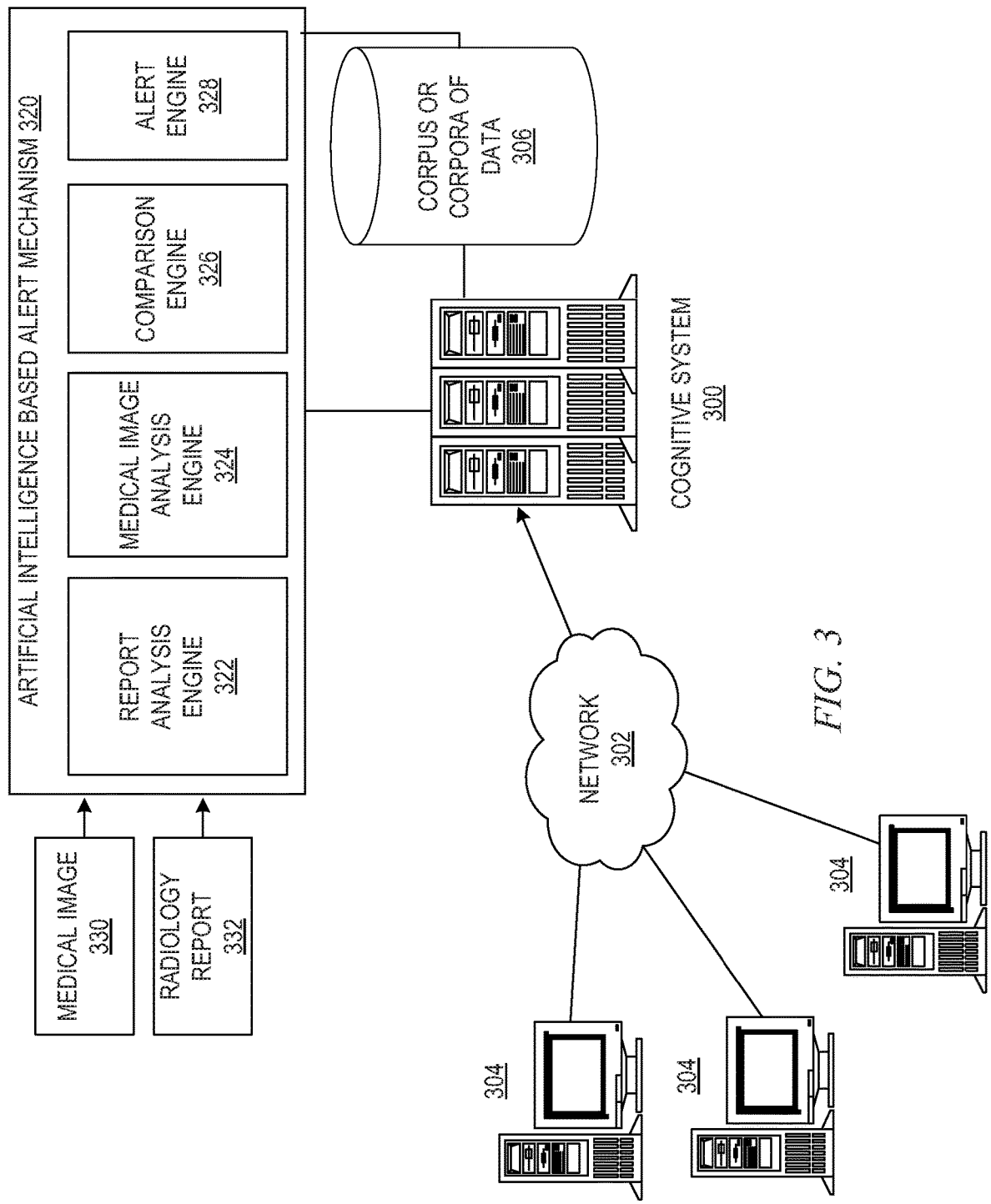
FIG. 3 is an example diagram illustrating an interaction of elements of a cognitive system in accordance with one illustrative embodiment.

The illustrative embodiments may be utilized in many different types of data processing environments. In order to provide a context for the description of the specific elements and functionality of the illustrative embodiments, FIGS. 1-3 are provided hereafter as example environments in which aspects of the illustrative embodiments may be implemented. It should be appreciated that FIGS. 1-3 are only examples and are not intended to assert or imply any limitation with regard to the environments in which aspects or embodiments of the present invention may be implemented. Many modifications to the depicted environments may be made without departing from the spirit and scope of the present invention.

FIGS. 1-3 are directed to describing an example cognitive system, i.e. an AI based alert system, for alerting a medical professional of potential inaccuracies in medical image analysis. The cognitive system implements a request processing pipeline, request processing methodology, and request processing computer program product with which the mechanisms of the illustrative embodiments are implemented. Received requests may be provided as structure or unstructured request messages, natural language questions, or any other suitable format for requesting an operation to be performed by the cognitive system. As described in more detail hereafter, the particular application that is implemented in the cognitive system of the present invention is an application for alerting a medical professional of potential inaccuracies in medical image analysis.

It should be appreciated that, the cognitive system, while shown as having a single request processing pipeline in the examples hereafter, may in fact have multiple request processing pipelines. Each request processing pipeline may be separately trained and/or configured to process requests associated with different domains or be configured to perform the same or different analysis on input requests, depending on the desired implementation. For example, in some cases, a first request processing pipeline may be trained to operate on input requests directed to analyzing a radiology report issued by a medical professional. In other cases, for example, a second request pipeline may be trained to analyze a same medical image associated with the radiology report in order to identify one or more diseases, conditions, or the like, associated with the medical image.

Moreover, each request processing pipeline may have its own associated corpus or corpora that, they ingest and operate on, e.g., one corpus for lung cancer domain related documents and another corpus for breast cancer domain related documents in the above examples. In some cases, the request processing pipelines may each operate on the same domain of input questions but may have different configurations, e.g., different annotators or differently trained annotators, such that different analysis and potential responses are generated. The cognitive system may provide additional logic for routing requests to the appropriate request processing pipeline, such as based on a determined domain of the input request, combining and evaluating final results generated by the processing performed by multiple request processing pipelines, and other control and interaction logic that facilitates the utilization of multiple request processing pipelines.

It should be appreciated that while the present invention will be described in the context of the cognitive system implementing one or more request processing pipelines that operate on a request, the illustrative embodiments are not limited to such. Rather, the mechanisms of the illustrative embodiments may operate on requests that are posed as "questions" or formatted as requests for the cognitive system to perform cognitive operations on a specified set of input data using the associated corpus or corpora and the specific configuration information used to configure the cognitive system.

As will be discussed in greater detail hereafter, the illustrative embodiments may be integrated in, augment, and extend the functionality of these QA pipeline, or request processing pipeline, mechanisms of a cognitive system with regard to alerting a medical professional of potential inaccuracies in medical image analysis. For example, after acquiring a medical image of a patient and a radiology report associated with the same medical image, the cognitive system analyzes the radiology reports using for example, a natural language processing (NLP) algorithm, to identify medical findings detected by the medical professional. The cognitive system also analyzes the medical image using for example, an image analytics algorithm, which is trained to detect diseases, conditions, or the like, associated with the particular medical image. Responsive to the cognitive system identifying one or more medical findings, the cognitive system compares the identified medical findings to those medical findings identified in the radiology report. Responsive to identifying a discrepancy in the two medical findings, the cognitive system generates an alert that is passed to the medical professional who generated the radiology report.

It should be appreciated that the mechanisms described in FIGS. 1-3 are only examples and are not intended to state or imply any limitation with regard to the type of cognitive system mechanisms with which the illustrative embodiments are implemented. Many modifications to the example cognitive system shown in FIGS. 1-3 may be implemented in various embodiments of the present invention without departing from the spirit and scope of the present invention.

As an overview, a cognitive system is a specialized computer system, or set of computer systems, configured with hardware and/or software logic (in combination with hardware logic upon which the software executes) to emulate human cognitive functions. These cognitive systems apply human-like characteristics to conveying and manipulating ideas which, when combined with the inherent strengths of digital computing, can solve problems with high accuracy and resilience on a large scale A cognitive system performs one or more computer-implemented cognitive operations that approximate a human thought process as well as enable people and machines to interact in a more natural manner so as to extend and magnify human expertise and cognition. A cognitive system comprises artificial intelligence logic, such as natural language processing (NLP) based logic, for example, and machine learning logic, which may be provided as specialized hardware, software executed on hardware, or any combination of specialized hardware and software executed on hardware. The logic of the cognitive system implements the cognitive operation(s), examples of which include, but are not limited to, question answering, identification of related concepts within different portions of content in a corpus, intelligent search algorithms, such as Internet web page searches, for example, medical diagnostic and treatment recommendations, and other types of recommendation generation, e.g., items of interest to a particular user, potential new contact recommendations, or the like.

IBM Watson™ is an example of one such cognitive system which can process human readable language and identify inferences between text passages with human-like high accuracy at speeds far faster than human beings and on a larger scale. In general, such cognitive systems are able to perform the following functions:

Navigate the complexities of human language and understanding,

Ingest and process vast amounts of structured and unstructured data,

Generate and evaluate hypothesis,

Weigh and evaluate responses that are based only on relevant evidence,

Provide situation-specific advice, insights, and guidance,

Improve knowledge and learn with each iteration and interaction through machine learning processes, Enable decision making at the point of impact (contextual guidance), Scale in proportion to the task, Extend and magnify human expertise and cognition, Identify resonating, human-like attributes and traits from natural language, Deduce various language specific or agnostic attributes from natural language, High degree of relevant recollection from data points (images, text, voice) (memorization and recall), Predict and sense with situational awareness that mimic human cognition based on experiences, or Answer questions based on natural language and specific evidence.

In one aspect, cognitive systems provide mechanisms for responding to requests posed to these cognitive systems using a request processing pipeline and/or process requests which may or may not be posed as natural language requests. The requests processing pipeline is an artificial intelligence application executing on data processing hardware that responds to requests pertaining to a given subject-matter domain presented in natural language. The request processing pipeline receives inputs from various sources including input over a network, a corpus of electronic documents or other data, data from a content creator, information from one or more content users, and other such inputs from other possible sources of input. Data storage devices store the corpus of data. A content creator creates content in a document for use as part of a corpus of data with the request processing pipeline. The document may include any file, text, article, or source of data for use in the requests processing system. For example, a request processing pipeline accesses a body of knowledge about the domain, or subject matter area, e.g., financial domain, medical domain, legal domain, etc., where the body of knowledge (knowledgebase) can be organized in a variety of configurations, e.g., a structured repository of domain-specific information, such as ontologies, or unstructured data related to the domain, or a collection of natural language documents about the domain.

Content users input requests to cognitive system which implements the request processing pipeline. The request processing pipeline then responds to the requests using the content in the corpus of data by evaluating documents, sections of documents, portions of data in the corpus, or the like. When a process evaluates a given section of a document for semantic content, the process can use a variety of conventions to query such document from the request processing pipeline, e.g., sending the query to the request processing pipeline as a well-formed requests which is then interpreted by the request processing pipeline and a response is provided containing one or more responses to the request. Semantic content is content based on the relation between signifiers, such as words, phrases, signs, and symbols, and what they stand for, their denotation, or connotation. In other words, semantic content is content that interprets an expression, such as by using Natural Language Processing.

As will be described in greater detail hereafter, the request processing pipeline receives a request, parses the request to extract the major features of the request, uses the extracted features to formulate queries, and then applies those queries to the corpus of data. Based on the application of the queries to the corpus of data, the request processing pipeline generates a set of responses to the request, by looking across the corpus of data for portions of the corpus of data that have some potential for containing a valuable response to the request. The request processing pipeline then performs deep analysis on the language of the request and the language used in each of the portions of the corpus of data found during the application of the queries using a variety of reasoning algorithms. There may be hundreds or even thousands of reasoning algorithms applied, each of which performs different analysis, e.g., comparisons, natural language analysis, lexical analysis, or the like, and generates a score. For example, some reasoning algorithms may look at the matching of terms and synonyms within the language of the request and the found portions of the corpus of data. Other reasoning algorithms may look at temporal or spatial features in the language, while others may evaluate the source of the portion of the corpus of data and evaluate its veracity.

As mentioned above, request processing pipeline mechanisms operate by accessing information from a corpus of data or information (also referred to as a corpus of content), analyzing it, and then generating answer results based on the analysis of this data. Accessing information from a corpus of data typically includes: a database query that answers requests about what is in a collection of structured records, and a search that delivers a collection of document links in response to a query against a collection of unstructured data (text, markup language, etc.). Conventional request processing systems are capable of generating answers based on the corpus of data and the input request, verifying answers to a collection of request for the corpus of data, correcting errors in digital text using a corpus of data, and selecting responses to requests from a pool of potential answers, i.e. candidate answers.

FIG. 1 depicts a schematic diagram of one illustrative embodiment of a cognitive system 100 implementing a request processing pipeline 108, which in some embodiments may be a request processing pipeline, in a computer network 102. For purposes of the present description, it will be assumed that the request processing pipeline 108 that operates on structured and/or unstructured requests in the form of requests. One example of a question processing operation which may be used in conjunction with the principles described herein is described in U.S. Patent Application Publication No. 2011/0125734, which is herein incorporated by reference in its entirety. The cognitive system 100 is implemented on one or more computing devices 104A-C (comprising one or more processors and one or more memories, and potentially any other computing device elements generally known in the art including buses, storage devices, communication interfaces, and the like) connected to the computer network 102. For purposes of illustration only, FIG. 1 depicts the cognitive system 100 being implemented on computing device 104A only, but as noted above the cognitive system 100 may be distributed across multiple computing devices, such as a plurality of computing devices 104A-C. The network 102 includes multiple computing devices 104A-C, which may operate as server computing devices, and 110 and 112 which may operate as client computing devices, in communication with each other and with other devices or components via one or more wired and/or wireless data communication links, where each communication link comprises one or more of wires, routers, switches, transmitters, receivers, or the like. In some illustrative embodiments, the cognitive system 100 and network 102 enables request processing functionality for one or more cognitive system users via their respective computing devices 110 and 112. In other embodiments, the cognitive system 100 and network 102 may provide other types of cognitive operations including, but not limited to, request processing and cognitive response generation which may take many different forms depending upon the desired implementation, e.g., cognitive information retrieval, training/instruction of users, cognitive evaluation of data, or the like. Other embodiments of the cognitive system 100 may be used with components, systems, sub-systems, and/or devices other than those that are depicted herein.

The cognitive system 100 is configured to implement a request processing pipeline 108 that receive inputs from various sources. The requests may be posed in the form of natural language request for information, natural language request for the performance of a cognitive operation, or the like. For example, the cognitive system 100 receives input from the network 102, a corpus or corpora of electronic documents 106, cognitive system users, and/or other data and other possible sources of input. In one embodiment, some or all of the inputs to the cognitive system 100 are routed through the network 102. The various computing devices 104A-D on the network 102 include access points for content creators and cognitive system users. Some of the computing devices 104A-C includes devices for a database storing the corpus or corpora of data 106 (which is shown as a separate entity in FIG. 1 for illustrative purposes only). Portions of the corpus or corpora of data 106 may also be provided on one or more other network attached storage devices, in one or more databases, or other computing devices not explicitly shown in FIG. 1. The network 102 includes local network connections and remote connections in various embodiments, such that the cognitive system 100 may operate in environments of any size, including local and global, e.g., the Internet.

In one embodiment, the content creator creates content in a document of the corpus or corpora of data 106 for use as part of a corpus of data with the cognitive system 100. The document includes any file, text, article, or source of data for use in the cognitive system 100. Cognitive system users access the cognitive system 100 via a network connection or an Internet connection to the network 102, and requests to the cognitive system 100 that are responded to/processed based on the content in the corpus or corpora of data 106. In one embodiment, the requests are formed using natural language. The cognitive system 100 parses and interprets the request via a pipeline 108, and provides a response to the cognitive system user, e.g., cognitive system user 110, containing one or more responses to the request posed, response to the request, results of processing the request, or the like. In some embodiments, the cognitive system 100 provides a response to users in a ranked list of candidate responses while in other illustrative embodiments, the cognitive system 100 provides a single final response or a combination of a final response and ranked listing of other candidate responses.

The cognitive system 100 implements the pipeline 108 which comprises a plurality of stages for processing a request based on information obtained from the corpus or corpora of data 106. The pipeline 108 generates responses for the request based on the processing of the request and the corpus or corpora of data 106. The pipeline 108 will be described in greater detail hereafter with regard to FIG. 3.

In some illustrative embodiments, the cognitive system 100 may be the IBM Watson™ cognitive system available from International Business Machines Corporation of Armonk, N.Y., which is augmented with the mechanisms of the illustrative embodiments described hereafter. As outlined previously, a pipeline of the IBM Watson™ cognitive system receives an input question or request which it then parses to extract the major features of the question/request, which in turn are then used to formulate queries that are applied to the corpus or corpora of data 106. Based on the application of the queries to the corpus or corpora of data 106, a set of hypotheses, or candidate answers/responses to the input question/request, are generated by looking across the corpus or corpora of data 106 for portions of the corpus or corpora of data 106 (hereafter referred to simply as the corpus 106) that have some potential for containing a valuable response to the input question/response (hereafter assumed to be an input question). The pipeline 108 of the IBM Watson™ cognitive system then performs deep analysis on the language of the input question and the language used in each of the portions of the corpus 106 found during the application of the queries using a variety of reasoning algorithms.

The scores obtained from the various reasoning algorithms are then weighted against a statistical model that summarizes a level of confidence that the pipeline 108 of the IBM Watson™ cognitive system 100, in this example, has regarding the evidence that the potential candidate answer is inferred by the question. This process is be repeated for each of the candidate answers to generate ranked listing of candidate answers which may then be presented to the user that submitted the input question, e.g., a user of client computing device 110, or from which a final answer is selected and presented to the user. More information about the pipeline 108 of the IBM Watson™ cognitive system 100 may be obtained, for example, from the IBM Corporation website, IBM Redbooks, and the like. For example, information about the pipeline of the IBM Watson™ cognitive system can be found in Yuan et al., "Watson and Healthcare," IBM developerWorks, 2011 and "The Era of Cognitive Systems: An Inside Look at IBM Watson and How it Works" by Rob High, IBM Redbooks, 2012.

As noted above, while the input to the cognitive system 100 from a client device may be posed in the form of a natural language question, the illustrative embodiments are not limited to such. Rather, the input question may in fact be formatted or structured as any suitable type of request which may be parsed and analyzed using structured and/or unstructured input analysis, including but not limited to the natural language parsing and analysis mechanisms of a cognitive system such as IBM Watson™, to determine the basis upon which to perform cognitive analysis and providing a result of the cognitive analysis. In the case of a healthcare based cognitive system, this analysis may involve processing patient medical records, medical guidance documentation from one or more corpora, and the like, to provide a healthcare oriented cognitive system result.

In the context of the present invention, cognitive system 100 may provide a cognitive functionality for alerting a medical professional of potential inaccuracies in medical image analysis. For example, depending upon the particular implementation, the healthcare based operations may comprise patient diagnostics, medical treatment recommendation systems, medical practice management systems, personal patient care plan generation and monitoring, patient electronic medical record (EMR) evaluation for various purposes, such as for identifying patients that are suitable for a medical trial or a particular type of medical treatment, or the like. Thus, the cognitive system 100 may be a cognitive system 100 that operates in the medical or healthcare type domains and which may process requests for such healthcare operations via the request processing pipeline 108 input as either structured or unstructured requests, natural language input questions, or the like. In one illustrative embodiment, the cognitive system 100 is an AI based alert system that alerts a medical professional of potential inaccuracies in medical image analysis.

As shown in FIG. 1, the cognitive system 100 is further augmented, in accordance with the mechanisms of the illustrative embodiments, to include logic implemented in specialized hardware, software executed on hardware, or any combination of specialized hardware and software executed on hardware, for implementing an AI based alert system 120 that generates an alert to a medical professional of potential inaccuracies in medical image analysis. Accordingly, as shown in FIG. 1, AI based alert system 120 comprises report analysis engine 122, medical image analysis engine 124, comparison engine 126, and alert engine 128.

AI based alert system 120 considers/represents a patient from a holistic point of view including non-image based information, such as demographics, family and medical history, lab results, radiology and other reports, or the like, as well as medical images that may manifest a particular medical malady. In order to identify a discrepancy between AI identified medical findings in a medical image and those medical findings identified in the radiology report associated with the same medical image, AI based alert system 120 acquires medical image 130 of a patient and radiology report 132 associated with medical image 130. Medical image 130 may be, for example, a computerized axial tomography (CT) scan, magnetic resonance imaging (MRI) scan, ultrasound (U/S) scan, positron emission tomography (PET) scan, X-ray scan, or the like. Radiology report 132 may be, for example, a radiology report interpreted by a radiologist per a standard of care. Report analysis engine 122 analyzes radiology report 132 using for example, various natural language processing (NLP) algorithms, deep learning algorithms, or other ways of extracting information from texts, to identify medical findings detected by the medical professional. Medical image analysis engine 124 analyzes medical image 130 to detect diseases, conditions, or the like, associated with the particular medical image. Medical image analysis engine 124 may use, for example, an image analytics algorithm, which is trained to detect diseases, conditions, or the like, associated with the particular medical image. For example, if the medical image is a mammography scan, then the image analytics algorithm is trained to detect diseases, conditions, or the like, associated with breast tissue. The image analysis algorithm may include but is not limited to Convolutional Neural Networks (CNNs). Long Short-Term Memory/Recurrent Neural Networks (LSTM/RNNs), or other machine learning algorithms. In analyzing the medical image, medical image analysis engine 124 may also reference the patient's electronic health record (EHR), non-image based information, such as demographics, family and medical history, lab results, radiology and other reports, or the like.

Responsive to medical image analysis engine 124 identifying one or more medical findings, comparison engine 126 compares the medical findings identified by medical image analysis engine 124 to those medical findings identified in radiology report 132. Responsive to comparison engine 126 identifying a discrepancy in the two medical findings, alert engine 128 generates an alert that is passed to the medical professional who generated the radiology report. The alerts may include but are not limited to a missing findings report, errors in interpretation of the images, errors in criticality level of findings, an email identifying the missing findings, a text message, automatic phone calls, or the like. The alert may include the original radiology report 132 and the medical findings identified by medical image analysis engine 124 along with the comparison of the medical findings making note of any discrepancies, or just the discrepancies between the medical findings identified by medical image analysis engine 124 to those medical findings identified in radiology report 132.

In one embodiment, implementing a review of radiology report by AI based alert system 120 occurs upon the medical professional signing off on radiology report 132 so as to directly impact the clinical care of the patient. In this implementation, the alert of any discrepancy would occur right after or fairly soon after the report is signed off. The medical professional would then have an opportunity to modify the findings in radiology report prior to be viewed by another medical professional. In another embodiment, implementing a review of radiology report by AI based alert system 120 occurs as part of a peer review workflow. Peer review is a quality control process where small portions of imaging studies are randomly selected to be reviewed by a second medical professional. This concept may be used for peer review to select studies that have a higher likelihood of containing a missed finding.

As noted above, the mechanisms of the illustrative embodiments are rooted in the computer technology arts and are implemented using logic present in such computing or data processing systems. These computing or data processing systems are specifically configured, either through hardware, software, or a combination of hardware and software, to implement the various operations described above. As such, FIG. 2 is provided as an example of one type of data processing system in which aspects of the present invention may be implemented. Many other types of data processing systems may be likewise configured to specifically implement the mechanisms of the illustrative embodiments.

FIG. 2 is a block diagram of an example data processing system in which aspects of the illustrative embodiments are implemented. Data processing system 200 is an example of a computer, such as server 104 or client 110 in FIG. 1, in which computer usable code or instructions implementing the processes for illustrative embodiments of the present invention are located. In one illustrative embodiment, FIG. 2 represents a server computing device, such as a server 104, which, which implements a cognitive system 100 and QA system pipeline 108 augmented to include the additional mechanisms of the illustrative embodiments described hereafter.

In the depicted example, data processing system 200 employs a hub architecture including North Bridge and Memory Controller Hub (NB/MCH) 202 and South Bridge and Input/Output (I/O) Controller Hub (SB/ICH) 204. Processing unit 206, main memory 208, and graphics processor 210 are connected to NB/MCH 202. Graphics processor 210 is connected to NB/MCH 202 through an accelerated graphics port (AGP).

In the depicted example, local area network (LAN) adapter 212 connects to SB/ICH 204. Audio adapter 216, keyboard and mouse adapter 220, modem 222, read only memory (ROM) 224, hard disk drive (HDD) 226, CD-ROM drive 230, universal serial bus (USB) ports and other communication ports 232, and PCI/PCIe devices 234 connect to SB/ICH 204 through bus 238 and bus 240. PCI/PCIe devices may include, for example, Ethernet adapters, add-in cards, and PC cards for notebook computers. PCI uses a card bus controller, while PCIe does not. ROM 224 may be, for example, a flash basic input/output system (BIOS).

HDD 226 and CD-ROM drive 230 connect to SB/ICH 204 through bus 240. HDD 226 and CD-ROM drive 230 may use, for example, an integrated drive electronics (IDE) or serial advanced technology attachment (SATA) interface. Super I/O (SIO) device 236 is connected to SB/ICH 204.

An operating system runs on processing unit 206. The operating system coordinates and provides control of various components within the data processing system 200 in FIG. 2. As a client, the operating system is a commercially available operating system such as Microsoft® Windows 10®). An object-oriented programming system, such as the Java™ programming system, may run in conjunction with the operating system and provides calls to the operating system from Java™ programs or applications executing on data processing system 200.

As a server, data processing system 200 may be, for example, an IBM® eServer™ System p® computer system, running the Advanced Interactive Executive (AIX®) operating system or the LINUX® operating system. Data processing system 200 may be a symmetric multiprocessor (SMP) system including a plurality of processors in processing unit 206. Alternatively, a single processor system may be employed.

Instructions for the operating system, the object-oriented programming system, and applications or programs are located on storage devices, such as HDD 226, and are loaded into main memory 208 for execution by processing unit 206. The processes for illustrative embodiments of the present invention are performed by processing unit 206 using computer usable program code, which is located in a memory such as, for example, main memory 208, ROM 224, or in one or more peripheral devices 226 and 230, for example.

A bus system, such as bus 238 or bus 240 as shown in FIG. 2, is comprised of one or more buses. Of course, the bus system may be implemented using any type of communication fabric or architecture that provides for a transfer of data between different components or devices attached to the fabric or architecture. A communication unit, such as modem 222 or network adapter 212 of FIG. 2, includes one or more devices used to transmit and receive data. A memory may be, for example, main memory 208, ROM 224, or a cache such as found in NB/MCH 202 in FIG. 2.

Those of ordinary skill in the art will appreciate that the hardware depicted in FIGS. 1 and 2 may vary depending on the implementation. Other internal hardware or peripheral devices, such as flash memory, equivalent non-volatile memory, or optical disk drives and the like, may be used in addition to or in place of the hardware depicted in FIGS. 1 and 2. Also, the processes of the illustrative embodiments may be applied to a multiprocessor data processing system, other than the SMP system mentioned previously, without departing from the spirit and scope of the present invention.

Moreover, the data processing system 200 may take the form of any of a number of different data processing systems including client computing devices, server computing devices, a tablet computer, laptop computer, telephone or other communication device, a personal digital assistant (PDA), or the like. In some illustrative examples, data processing system 200 may be a portable computing device that is configured with flash memory to provide non-volatile memory for storing operating system files and/or user-generated data, for example. Essentially, data processing system 200 may be any known or later developed data processing system without architectural limitation, FIG. 3 is an example diagram illustrating an interaction of elements of a cognitive system in accordance with one illustrative embodiment. The example diagram of FIG. 3 depicts an implementation of a cognitive system 300, which may be a cognitive system such as cognitive system 100 described in FIG. 1, that is configured to alert a medical professional of potential inaccuracies in medical image analysis. However, it should be appreciated that this is only an example implementation and other healthcare operations may be implemented in other embodiments of the cognitive system 300 without departing from the spirit and scope of the present invention.

As shown in FIG. 3, in accordance with one illustrative embodiment, cognitive system 300 receives input data in the way of medical image 330 of a patient and radiology report 332 associated with medical image 330 from one or more computing device 304 via a network 302. Medical image 330 may be, for example, a computerized axial tomography (CT) scan, magnetic resonance imaging (MRI) scan, ultrasound (U/S) scan, positron emission tomography (PET) scan, X-ray scan, or the like. Radiology report 332 may be, for example, a radiology report interpreted by a radiologist per a standard of care. In accordance with the illustrative embodiments herein, cognitive system 300 is augmented to include AI based alert system 320. AI based alert system 320 comprises report analysis engine 322, medical image analysis engine 324, comparison engine 326, and alert engine 328.

In order to identify a discrepancy between AI identified medical findings in a medical image and those medical findings identified in the radiology report associated with the same medical image, report analysis engine 122 analyzes radiology report 132 using for example, a various natural language processing (NLP) algorithms, deep learning algorithms, or other ways of extracting information from texts to identify medical findings detected by the medical professional. Medical image analysis engine 324 then analyzes medical image 330 to detect diseases, conditions, or the like, associated with the particular medical image. Medical image analysis engine 324 may use, for example, an image analytics algorithm, which is trained to detect diseases, conditions, or the like, associated with the particular medical image. For example, if the medical image is a mammography scan, then the image analytics algorithm is trained to detect diseases, conditions, or the like, associated with breast tissue. The image analysis algorithm may include but is not limited to Convolutional Neural Networks (CNNs), Long Short-Term Memory/Recurrent Neural Networks (LSTM/RNNs), or other machine learning algorithms. In analyzing the medical image, medical image analysis engine 324 may also reference the patient's electronic health record (EHR), non-image based information, such as demographics, family and medical history, lab results, radiology and other reports, or the like.

Responsive to medical image analysis engine 324 identifying one or more medical findings, comparison engine 326 compares the medical findings identified by medical image analysis engine 324 to those medical findings identified in radiology report 332. Responsive to comparison engine 326 identifying a discrepancy in the two medical findings, alert engine 328 generates an alert that is passed to the medical professional who generated the radiology report. The alerts may include but are not limited to a missing findings report, errors in interpretation of the images, errors in criticality level of findings, an email identifying the missing findings, a text message, automatic phone calls, or the like. The alert may include the original radiology report 332 and the medical findings identified by medical image analysis engine 324 along with the comparison of the medical findings making note of any discrepancies, or just the discrepancies between the medical findings identified by medical image analysis engine 324 to those medical findings identified in radiology report 332.

In one embodiment, implementing a review of radiology report by AI based alert system 320 occurs upon the medical professional signing off on radiology report 332 so as to directly impact the clinical care of the patient. In this implementation, the alert of any discrepancy would occur right after or fairly soon after the report is signed off. The medical professional would then have an opportunity to modify the findings in radiology report prior to be viewed by another medical professional. In another embodiment, implementing a review of radiology report by AI based alert system 320 occurs as part of a peer review workflow. Peer review is a quality control process where small portions of imaging studies are randomly selected to be reviewed by a second medical professional. This concept may be used for peer review to select studies that have a higher likelihood of containing a missed finding.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Java, Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement, the functions/acts specified in the flowchart and/or block diagram block or blocks.

Figure 4:
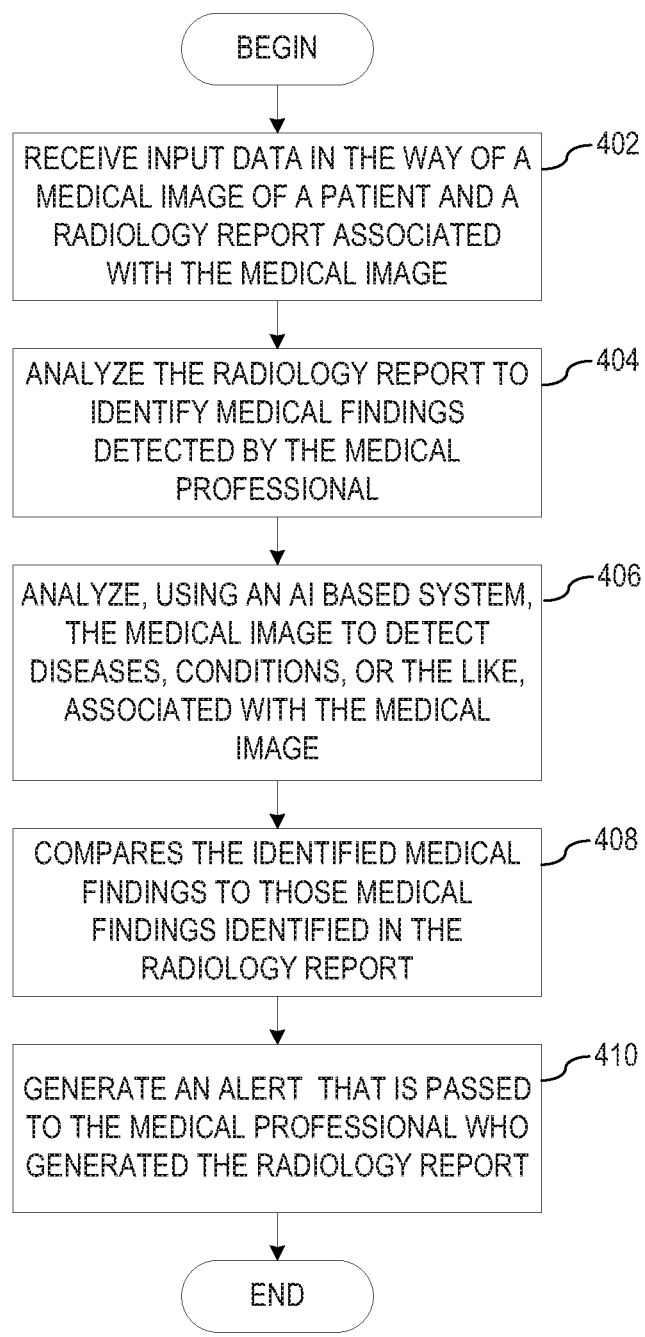
FIG. 4 depicts an exemplary flowchart of the operation performed by a cognitive system in implementing an artificial intelligence (AI) based alert mechanism that alerts a medical professional of potential inaccuracies in medical image analysis in accordance with an illustrative embodiment.

FIG. 4 depicts an exemplary flowchart of the operation performed by a cognitive system, such as cognitive system 300 in FIG. 3 or an implementation of cognitive system 100 in FIG. 1, in implementing an artificial intelligence (AI) based alert mechanism that alerts a medical professional of potential inaccuracies in medical image analysis in accordance with an illustrative embodiment. As the operation begins, AI based alert mechanism receives input data in the way of a medical image of a patient and a radiology report associated with the medical image (step 402). The medical image may be, for example, a computerized axial tomography (CT) scan, magnetic resonance imaging (MRI) scan, ultrasound (U/S) scan, positron emission tomography (PET) scan, X-ray scan, or the like. The radiology report may be, for example, a radiology report interpreted by a radiologist per a standard of care. In order to identify a discrepancy between AI identified medical findings in a medical image and those medical findings identified in the radiology report associated with the same medical image, the AI based alert mechanism analyzes the radiology report using, for example, various natural language processing (NLP) algorithms, deep learning algorithms, or other ways of extracting information from texts to identify medical findings detected by the medical professional (step 404).

The AI based alert mechanism then analyzes the medical image to detect diseases, conditions, or the like, associated with the particular medical image (step 406). The AI based alert mechanism may use, for example, an image analytics algorithm, which is trained to detect diseases, conditions, or the like, associated with the particular medical image. For example, if the medical image is a mammography scan, then the image analytics algorithm is trained to detect diseases, conditions, or the like, associated with breast tissue. The image analysis algorithm may include but is not limited to Convolutional Neural Networks (CNNs), Long Short-Term Memory/Recurrent Neural Networks (LSTM/RNNs), or other machine learning algorithms. In analyzing the medical image, the AI based alert mechanism may also reference the patient's electronic health record (EHR), non-image based information, such as demographics, family and medical history, lab results, radiology and other reports, or the like.

Responsive to the AI based alert mechanism identifying one or more medical findings, the AI based alert mechanism compares the identified medical findings to those medical findings identified in the radiology report (step 408). Responsive to the AI based alert mechanism identifying a discrepancy in the two medical findings, the AI based alert mechanism generates an alert that is passed to the medical professional who generated the radiology report (step 410). The alerts may include but are not limited to a missing findings report, errors in interpretation of the images, errors in criticality level of findings, an email identifying the missing findings, a text message, automatic phone calls, or the like. The alert may include the original radiology report and the medical findings identified by the AI based alert mechanism along with the comparison of the medical findings making note of any discrepancies, or just the discrepancies between the medical findings identified by the AI based alert mechanism to those medical findings identified in the radiology report. The operation terminates thereafter.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Thus, the illustrative embodiments provide mechanisms for alerting a medical professional of potential inaccuracies in medical image analysis. In the illustrative embodiments, the AI based alert mechanism acquires a medical image of a patient and a radiology report associated with the same medical image, such as a radiology report interpreted by a radiologist per a standard of care. The AI based alert mechanism analyzes the radiology reports using for example, an natural language processing (NLP) algorithm, to identify medical findings detected by the medical professional. The AI based alert mechanism further analyzes the same medical image using, for example, an image analytics algorithm, which is trained to detect diseases, conditions, or the like, associated with the particular medical image. Responsive to the AI based alert mechanism identifying one or more medical findings, the AI based alert mechanism compares the AI identified medical findings to those medical findings identified in the radiology report Responsive to identifying a discrepancy in the two medical findings, the AI based alert mechanism generates an alert that is passed to the medical professional who generated the radiology report. Thus, the AI based alert mechanism identifies potential inaccuracies in medical image analysis using a combination of AI medical image analysis and radiology report analysis.

As noted above, it should be appreciated that the illustrative embodiments may take the form of an entirely hardware embodiment, an entirely software embodiment or an embodiment containing both hardware and software elements. In one example embodiment, the mechanisms of the illustrative embodiments are implemented in software or program code, which includes but is not limited to firmware, resident software, microcode, etc.

A data processing system suitable for storing and/or executing program code will include at least one processor coupled directly or indirectly to memory elements through a communication bus, such as a system bus, for example. The memory elements can include local memory employed during actual execution of the program code, bulk storage, and cache memories which provide temporary storage of at least some program code in order to reduce the number of times code must be retrieved from bulk storage during execution. The memory may be of various types including, but not limited to, ROM, PROM, EPROM, EEPROM, DRAM, SRAM, Flash memory, solid state memory, and the like.

Input/output or I/O devices (including but not limited to keyboards, displays, pointing devices, etc.) can be coupled to the system either directly or through intervening wired or wireless I/O interfaces and/or controllers, or the like. I/O devices may take many different forms other than conventional keyboards, displays, pointing devices, and the like, such as for example communication devices coupled through wired or wireless connections including, but not limited to, smart phones, tablet computers, touch screen devices, voice recognition devices, and the like. Any known or later developed I/O device is intended to be within the scope of the illustrative embodiments.

Network adapters may also be coupled to the system to enable the data processing system to become coupled to other data processing systems or remote printers or storage devices through intervening private or public networks. Modems, cable modems and Ethernet cards are just a few of the currently available types of network adapters for wired communications. Wireless communication based network adapters may also be utilized including, but not limited to, 802.11 a/b/g/n wireless communication adapters, Bluetooth wireless adapters, and the like. Any known or later developed network adapters are intended to be within the spirit and scope of the present invention.

The description of the present invention has been presented for purposes of illustration and description, and is not intended to be exhaustive or limited to the invention in the form disclosed. Many modifications and variations will be apparent to those of ordinary skill in the art without departing from the scope and spirit of the described embodiments. The embodiment was chosen and described in order to best explain the principles of the invention, the practical application, and to enable others of ordinary skill in the art to understand the invention for various embodiments with various modifications as are suited to the particular use contemplated. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method, in a data processing system comprising at least one processor and at least one memory, the at least one memory comprising instructions executed by the at least one processor to cause the at least one processor to implement an artificial intelligence (AI) based alert mechanism system for alerting a medical professional of potential inaccuracies in medical image analysis, wherein the AI based alert mechanism system operates to:
   receiving, by the AI based alert mechanism, a medical image of a patient and a radiology report associated with the medical image;
   analyzing, by the AI based alert mechanism, the radiology report to identify medical findings detected by the medical professional;
   analyzing, by the AI based alert mechanism, the medical image to detect one or more medical findings associated with the medical image;
   responsive to the AI based alert mechanism detecting one or more medical findings associated with the medical image, comparing, by the AI based alert mechanism, the one or more medical findings associated with the medical image to those medical findings detected by the medical professional and identified in the radiology report; and
   responsive to the AI based alert mechanism identifying a discrepancy between the detected medical findings associated with the medical image to those medical findings detected by the medical professional and identified in the radiology report, generating, by the AI based alert mechanism, an alert to the medical professional who generated the radiology report, wherein the alert identifies missing medical findings in the radiology report, errors in interpretation of the medical image, and errors in a criticality level of the medical findings detected by the medical professional and identified in the radiology report.

2. The method of claim 1, wherein the medical image is selected from the group consisting of a computerized axial tomography (CT) scan, magnetic resonance imaging (MRI) scan, ultrasound (U/S) scan, positron emission tomography (PET) scan, or X-ray scan.

3. The method of claim 1, wherein analyzing the radiology report comprises the use of natural language processing (NLP).

4. The method of claim 1, wherein analyzing the medical image to detect one or more medical findings associated with the medical image comprises the use of an image analytics algorithm trained to detect diseases or conditions associated with the medical image.

5. The method of claim 1, wherein analyzing the medical image to detect one or more medical findings associated with the medical image further comprises:
   analyzing, by the AI based alert mechanism, one or more of the patient's electronic health record (EHR), non-image based information, demographics, family history, medical history, lab results, or other radiology reports.

6. The method of claim 1, wherein the alert comprises one or more of the radiology report, the one or more medical findings associated with the medical image detected by the AI based alert mechanism, the comparison making note of any discrepancies between the detected medical findings associated with the medical image to those medical findings detected by the medical professional and identified in the radiology report.

7. The method of claim 1, wherein the receiving, analyzing, analyzing, comprising, and generating occur upon the medical professional signing off on the radiology report so as to directly impact the clinical care of the patient.

8. The method of claim 1, wherein the receiving, analyzing, analyzing, comprising, and generating occur as part of a peer review workflow.

9. A computer program product comprising a non-transitory computer readable storage medium having a computer readable program stored therein, wherein the computer readable program, when executed on a data processing system, causes the data processing system to implement an artificial intelligence (AI) based alert mechanism system for alerting a medical professional of potential inaccuracies in medical image analysis, and further causes the data processing system to:
   receive, by the AI based alert mechanism, a medical image of a patient and a radiology report associated with the medical image;
   analyze, by the AI based alert mechanism, the radiology report to identify medical findings detected by the medical professional;
   analyze, by the AI based alert mechanism, the medical image to detect one or more medical findings associated with the medical image;
   responsive to the AI based alert mechanism detecting one or more medical findings associated with the medical image, compare, by the AI based alert mechanism, the one or more medical findings associated with the medical image to those medical findings detected by the medical professional and identified in the radiology report; and responsive to the AI based alert mechanism identifying a discrepancy between the detected medical findings associated with the medical image to those medical findings detected by the medical professional and identified in the radiology report, generate, by the AI based alert mechanism, an alert to the medical professional who generated the radiology report, wherein the alert identifies missing medical findings in the radiology report, errors in interpretation of the medical image, and errors in a criticality level of the medical findings detected by the medical professional and identified in the radiology report.

10. The computer program product of claim 9, wherein the medical image is selected from the group consisting of a computerized axial tomography (CT) scan, magnetic resonance imaging (MRI) scan, ultrasound (U/S) scan, positron emission tomography (PET) scan, or X-ray scan.

11. The computer program product of claim 9, wherein analyzing the radiology report comprises the use of natural language processing (NLP).

12. The computer program product of claim 9, wherein analyzing the medical image to detect one or more medical findings associated with the medical image comprises the use of an image analytics algorithm trained to detect diseases or conditions associated with the medical image.

13. The computer program product of claim 9, wherein the computer readable program to analyze the medical image to detect one or more medical findings associated with the medical image further causes the data processing system to:

analyze, by the AI based alert mechanism, one or more of the patient's electronic health record (EHR), non-image based information, demographics, family history, medical history, lab results, or other radiology reports.

14. The computer program product of claim 9, wherein the alert comprises one or more of the radiology report, the one or more medical findings associated with the medical image detected by the AI based alert mechanism, the comparison making note of any discrepancies, between the detected medical findings associated with the medical image to those medical findings detected by the medical professional and identified in the radiology report.

15. A data processing system comprising:
at least one processor; and
at least one memory coupled to the at least one processor, wherein the at least one memory comprises instructions which, when executed by the at least one processor, cause the at least one processor to implement an artificial intelligence (AI) based alert mechanism system for alerting a medical professional of potential inaccuracies in medical image analysis, and further cause the at least one processor to:
receive, by the AI based alert mechanism, a medical image of a patient and a radiology report associated with the medical image;

analyze, by the AI based alert mechanism, the radiology report to identify medical findings detected by the medical professional;

analyze, by the AI based alert mechanism, the medical image to detect one or more medical findings associated with the medical image;

responsive to the AI based alert mechanism detecting one or more medical findings associated with the medical image, compare, by the AI based alert mechanism, the one or more medical findings associated with the medical image to those medical findings detected by the medical professional and identified in the radiology report; and responsive to the AI based alert mechanism identifying a discrepancy between the detected medical findings associated with the medical image to those medical findings detected by the medical professional and identified in the radiology report, generate, by the AI based alert mechanism, an alert to the medical professional who generated the radiology report, wherein the alert identifies missing medical findings in the radiology report, errors in interpretation of the medical image, and errors in a criticality level of the medical findings detected by the medical professional and identified in the radiology report.

16. The data processing system of claim 15, wherein the medical image is selected from the group consisting of a computerized axial tomography (CT) scan, magnetic resonance imaging (MRI) scan, ultrasound (U/S) scan, positron emission tomography (PET) scan, or X-ray scan.

17. The data processing system of claim 15, wherein analyzing the radiology report comprises the use of natural language processing (NLP).

18. The data processing system of claim 15, wherein analyzing the medical image to detect one or more medical findings associated with the medical image comprises the use of an image analytics algorithm trained to detect diseases or conditions associated with the medical image.

19. The data processing system of claim 15, wherein the instructions to analyze the medical image to detect one or more medical findings associated with the medical image further cause the at least one processor to:
analyze, by the AI based alert mechanism, one or more of the patient's electronic health record (EHR), non-image based information, demographics, family history, medical history, lab results, or other radiology reports.

20. The data processing system of claim 15, wherein the alert comprises one or more of the radiology report, the one or more medical findings associated with the medical image detected by the AI based alert mechanism, the comparison making note of any discrepancies between the detected medical findings associated with the medical image to those medical findings detected by the medical professional and identified in the radiology report.

* * * * *